(12) United States Patent
Weise et al.

(10) Patent No.: US 11,690,500 B2
(45) Date of Patent: Jul. 4, 2023

(54) STEREO-ENDOSCOPE

(71) Applicant: avateramedical GmbH, Jena (DE)

(72) Inventors: Fabian Weise, Berlin (DE); Stefan Beyer, Berlin (DE)

(73) Assignee: avateramedical GmbH, Jena (DE)

( * ) Notice: Subject to any disclaimer, the term of this patent is extended or adjusted under 35 U.S.C. 154(b) by 0 days.

(21) Appl. No.: 17/367,109

(22) Filed: Jul. 2, 2021

(65) Prior Publication Data

US 2022/0021807 A1    Jan. 20, 2022

(30) Foreign Application Priority Data

Jul. 16, 2020  (DE) .......................... 102020118814.5

(51) Int. Cl.
*A61B 1/00*        (2006.01)
*A61B 1/06*        (2006.01)
(Continued)

(52) U.S. Cl.
CPC ...... *A61B 1/00193* (2013.01); *A61B 1/00009* (2013.01); *A61B 1/00096* (2013.01); *A61B 1/046* (2022.02); *A61B 1/063* (2013.01); *A61B 1/0638* (2013.01); *A61B 1/0676* (2013.01); *H04N 23/80* (2023.01); *H04N 23/555* (2023.01)

(58) Field of Classification Search
CPC ........ H04N 5/23229; H04N 2005/2255; A61B 1/00096; A61B 1/063; A61B 1/0638; A61B 1/0676; A61B 1/00009; A61B 1/00186; A61B 1/00188; A61B 1/042; A61B 1/043; A61B 1/046; A61B 1/00193; A61B 1/00064; A61B 1/00131; A61B 1/00163;
(Continued)

(56) References Cited

U.S. PATENT DOCUMENTS 5,522,789 A   6/1996  Takahashi
5,776,049 A   7/1998  Takahashi
(Continued)

FOREIGN PATENT DOCUMENTS

WO   WO 2015/023990 A1   2/2015
WO   WO 2015/126466 A1   8/2015
WO   WO 2020/061104 A1   3/2020

*Primary Examiner* — Nasim N Nirjhar
(74) *Attorney, Agent, or Firm* — Christensen, Fonder, Dardi & Herbert PLLC (57) ABSTRACT

A stereo-endoscope for observation and analysis of an object, comprising a shaft with distal and proximal ends, illuminating means for illuminating the object, and stereoscopic imaging means which transfer light radiated by the object from the distal end to the proximal end. Light of a first imaging channel is fed into a first sensor, and light of a second imaging channel is fed into a second sensor. Both sensors contain mutually different beam splitters, which split the light into four light beams. One light beam from each of the sensors is deflected onto one sensor each; these two sensors are identical. The signals detected there are assembled to form a stereoscopic image. The stereo-endoscope comprises mutually different manipulating means for the other two light beams; by means of suitably-tuned image-processing algorithms, two different monoscopic images containing information complementary to each other and to the stereoscopic image are generated.

15 Claims, 4 Drawing Sheets

(51) Int. Cl.
*A61B 1/04* (2006.01)
*H04N 23/80* (2023.01)
*H04N 23/50* (2023.01)

(58) Field of Classification Search
CPC ........ A61B 1/0684; A61B 1/07; G01N 21/65;
G02B 23/2461; G02B 23/2484
See application file for complete search history.

(56) References Cited

U.S. PATENT DOCUMENTS

| | | |
|---|---|---|
| 8,169,468 B2 | 5/2012 | Scott et al. |
| 2010/0056928 A1* | 3/2010 | Zuzak .................. G01J 3/10 356/302 |
| 2012/0105611 A1* | 5/2012 | Godar ................ H04N 13/366 348/54 |
| 2012/0200829 A1* | 8/2012 | Bronstein .......... H04N 5/22541 348/340 |
| 2014/0375789 A1* | 12/2014 | Lou ..................... G06F 3/013 348/78 |
| 2015/0042774 A1 | 2/2015 | Sugano et al. |
| 2017/0090584 A1* | 3/2017 | Tang ................... G06V 40/113 |
| 2019/0200848 A1* | 7/2019 | McDowall ............ G06V 20/20 |
| 2020/0093357 A1 | 3/2020 | Scott et al. |
| 2022/0138998 A1* | 5/2022 | Rege ................... G02B 25/001 345/633 |
| 2022/0217320 A1* | 7/2022 | Maleki ................ H04N 13/261 |

* cited by examiner

STEREO-ENDOSCOPE

PRIORITY CLAIM

The present application claims priority to German Patent Application No. 10 2020 118 814.5, filed on Jul. 16, 2020, which said application is incorporated by reference in its entirety herein.

FIELD OF THE INVENTION

The invention relates to a stereo-endoscope for the observation an analysis of an object. Such a stereo-endoscope comprises a shaft with a distal end and a proximal end. Furthermore it comprises illuminating means or device which illuminate the object from the distal end of the shaft, and stereoscopic imaging means which transmit light radiated by the object from the distal end to the proximal end. Further constituents of the stereo-endoscopes form a first and a second sensor unit. On the first sensor unit, light from a first imaging channel is image d. The said first sensor unit comprises a first beam splitter, which splits the light into a first light beam and a second light beam. The first sensor unit furthermore comprises a first and a second sensor. The first sensor detects the light of the first light beam and converts it into first electromagnetic signals. The second sensor detects light of the second light beam and converts it into second electromagnetic signals. Light from a second imaging channel is image d onto the second sensor unit. The second sensor unit comprises a second beam splitter, which splits the light into a third light beam and a fourth light beam. The second sensor unit further comprises a third and a fourth sensor. The third sensor detects light from the third light beam and converts it into third electromagnetic signals. The fourth sensor detects light from the fourth light beam and converts it into fourth electromagnetic signals. The second sensor and the third sensor are of the same kind and detect light in the visible spectral region. Finally, the stereo-endoscope comprises an image processing unit for processing the first, second, third and fourth electromagnetic signals. In this process, the second and third electromagnetic signals are processed by the image processing unit into a stereoscopic image.

BACKGROUND OF THE INVENTION

In prior art, a number of stereo-endoscopes are known, some of which are combined with various image processing techniques. U.S. Pat. No. 5,776,049 A describes a stereo-endoscope in which, by means of identical transmittance systems, the images for the left and the right channel are transmitted through the shaft of the stereo-endoscope from the distal to the proximal end where they, having passed through appropriate imaging optics, are image d on flat-panel array detectors.

US 2019/0200848 A1 describes a stereo-endoscope as part of a robotic surgery system, which enables the capture of stereoscopic images in the visible region on the one hand, and hyperspectral stereoscopic images on the other hand. For hyperspectral image s, a wavelength region, which may especially comprise wavelengths also of other than visible wavelength regions, is split up into a multitude of narrow spectral channels. For each spectral channel, a separate image is taken so that one obtains, at the end, a data cube or a three-dimensional data matrix, in which, for each pixel of an area sensor, the images taken through the various spectral channels are saved. In US 2019/0200848 A1, the hyperspectral data are used to generate augmented images, i.e., improved-quality stereoscopic images in the visible range, supplemented by information from the hyperspectral data, e.g., in order to emphasize certain symptoms or structures in the tissue observed, which would hardly be noticeable with visible light alone.

Another possibility to emphasize certain signs in the tissue consists in the excitation and detection of fluorescence. An optical system that implements this and may be configured, e.g., as an endoscope, is described in WO 2015/023990 A1. The optical system comprises, on the one hand, a hyperspectral camera and, on the other hand, and an additional light source by means of which fluorescence can be excited. Thus equipped, the system can alternatingly record: (1) customary hyperspectral images through all color channels available—images that reproduce the natural colors of the tissue, based on their chromophores, and (2) images limited to specific color channels to record, e.g., fluorescence signals. As an example, the dye ICG (indocyanine green) is mentioned, which is administered intravenously to mark live tissues. When irradiated with excitation light in a wavelength range between 600 nm and 900 nm, ICG can be used to emit fluorescence in the near infrared wavelength range between 750 nm and 950 nm. An emission maximum for ICG dissolved in blood is at about 830 nm. ICG used, e.g., in tumor diagnostics for minimal-invasive examinations of the regional state of lymph nodes.

While with the stereo-endoscope described in US 2019/0200848 A1 it is possible to generate augmented stereo images that have a higher information content than images recorded merely in the visual range, there are situations, though, in which it would be desirable to have yet more analysis and/or imaging methods available in the endoscope for a more detailed analysis of the tissue examined.

SUMMARY OF THE INVENTION

Departing from this/therefrom, the problem of the invention is to develop a stereo-endoscope that, compared to prior art, offers improved facilities to display augmented images yielding added information.

For a stereo-endoscope of the type outlined above, this problem is solved by the following additional features: In the first sensor unit, first manipulating means intended for manipulating the first light beam are arranged between the first beam splitter and the first sensor. Analogously, in the second sensor unit, second manipulating means differing from the first manipulating means and intended for manipulating the fourth light beam are arranged between the second beam splitter and the fourth sensor. Implemented in the image processing unit is a first image processing algorithm tuned to the first manipulating means, and a second image processing algorithm tuned to the second manipulating means. The first image processing algorithm generates a first monoscopic image, and the second image processing algorithm generates a second monoscopic image. Here, the first and second manipulating means, the first and fourth sensors and the first and second image processing algorithms are specified in such a way that the first and the second monoscopic and the stereoscopic image contain complementary image information.

Here, the term, "complementary image information" is understood to describe bits of information that supplement each other. This means that the first monoscopic image contains information that goes beyond the image information of the stereoscopic image and is not contained in the latter, whereas the second monoscopic image contains further information that is contained neither in the first monoscopic image nor in the stereoscopic image. Thus, methods that yield complementary image information are basically complementary. Moreover, the complementary methods may also differ in other properties, such as, e.g., the time required for recording the image. Hyperspectral analysis methods, e.g., yield precise information enabling the determination of tissue parameters, but are relatively time-consuming. By contrast, the analysis of fluorescence images, i.e. of images of a sample of live tissue first marked with fluorescence markers, is fast and, depending on the marker, yields specific information about the location of a kind of tissue in the sample. In principle, the availability of several complementary methods in an endoscope gives a surgeon more imaging options, which permits him/her to adapt to a wide variety of patient situations. The surgeon can, for example, make allowance for the incompatibility of particular medicaments, etc.

In addition to the stereoscopic image, which can be represented visually and, as a rule, is recorded in the visible wavelength range, monoscopic images are recorded by two more, mutually complementary methods. The two imaging channels, which are combined for the stereoscopic image, are allocated to different examination or imaging methods.

Usually, every examination or imaging method requires its own manipulating means. In the simplest case, these are understood to be optical elements such as filters or lenses, but also prisms for spectral dispersion, or more complex manipulating means, such as those required, e.g., for recording hyperspectral image s. With more complex methods, the manipulating means may also manipulate the light beam used for illumination, e.g., by polarization, for which purpose it is expedient to configure illuminating means in such a way that the illuminating light is also coupled out from the sensor unit via a suitable beam splitter, e.g., the first or the second beam splitter or an extra beam splitter, and coupled into the shaft, which, as a rule, houses a transmission system. In such cases, the sensor unit can be called a sensor-cum-manipulation unit.

In prior art, image processing algorithms specially adapted to various recording and analysis methods are usually available. By means of also known image processing algorithms, the monoscopic images recorded can then be used to improve the quality of the stereoscopic image by the information from the former being superimposed on the latter. It is not necessary, for that purpose, to stereoscopically record also those images which are generated by means of the first and second manipulating means. By means of an appropriate image processing algorithm, one can make sure that the superimposed information from the monoscopic images does not spoil the stereoscopic overall impression of the image recorded in the visual range.

In the simplest case, the illuminating device or means comprise a single light source, e.g., an LED, but preferably several light sources which are preferably tuned to the manipulating means. If, for example, one intends to excite fluorescence, the light source needs to radiate light by which fluorescence can be excited. Therefore one can use, e.g., an LED radiating incoherent light. Preferably, the illuminating means comprise at least one first and one second light source, with at least one of the light source preferably radiating monochromatic and coherent light, i.e., it is configured as a laser light source. The use of laser light sources provides access to many more analysis methods.

By way of example, the first and second manipulating means, the first and fourth sensors and the first and second image processing algorithms are adapted for generating (i.) a fluorescence image from fluorescence signals, (ii.) a hyperspectral image, (iii.), a polarization-resolved image, (iv.) a Raman spectroscopy image, (v.) an optical coherence tomography image, (vi.) a speckle contrast image (vii.), a multiband image, or (viii.) a narrowband image.

For the generation of a Raman spectroscopy image, the appropriate manipulating means would have to comprise a spectrometer optimized for accordingly higher wavelengths. In the case of a narrowband image, one would use a light source radiating in one or several narrowband spectral regions; for detection, the manipulating means in front of the image sensor would comprise a band-pass filter. Both measures can be used alternatively or in combination.

For the generation of a polarization-resolved image, a number of means are eligible. For example, the respective light source can be provided with a polarizer. If the light is directed to the distal end through a light guide fiber, the polarizer may be arranged, e.g., at the point at which the light exits from the light guide fiber. Where appropriate, non-polarized light can be used for illumination. For detection one can use flat-panel array detectors with polarizing filters arranged in front of them. Another possibility is to provide the flat-panel array detector with a polarizing pattern, with a group of pixels determining the polarizing state similarly to color determination by Bayer patterns with a normal camera detecting in the colors red, green, and blue.

For the generation of a Speckle contrast image, illumination can be by a laser wavelength outside the visible spectrum; in that case, imaging for the stereoscopic image can take place simultaneously with imaging in the visual region.

For recording an optical coherence tomography image, one uses an appropriate sensor unit which comprises, among other devices, an interferometer, where the illuminating light is superimposed on the light backscattered by the object. Coherent illumination can be implemented via the imaging optics. The various scanners of the OCT-module need not be arranged in the sensor unit but can be located, e.g., in the endoscope body (also called endoscope housing). Connection to the coherent light source and to the interferometer would be by light guide fibers. The light source can be arranged outside the endoscope.

It would be expedient for the first and the second beam splitter to be of different configurations, in order to achieve greater flexibility in using different methods and/or manipulating means.

In a particularly preferred embodiment, the first manipulating means, the first sensor and the first image processing algorithm are adapted to generating a fluorescence image from fluorescence signals, and the first sensor is adapted to detecting the corresponding fluorescence spectrum. The marker used can be ICG, for example; in this case, the first manipulating means, the first sensor and the first image processing algorithm must process fluorescence signals in the infrared region. As the fluorescence of ICG is outside the visible region, the stereoscopic image recorded in the visible wavelength range will not be interfered with. Superimposition is possible, nevertheless, if the regions emitting fluorescence are represented in false color mode afterwards. The superimposition may take place without depth resolution; then, each of the two channels, or also on one of the channels only, will display the same information for ICG. On the basis of the optical data and the depth information from the stereoscopic record, this monoscopic image can, however, be converted into a stereoscopic image. In that way, the various tissue kinds can be better differentiated, allowing better assessment of the necessary scope of tumor resection. Instead of ICG it is possible, of course, to use other fluorescence markers, such as methylene blue, with manipulation means and sensors tuned accordingly; this can contribute to improved differentiation of tissue kinds.

With particular preference, the second manipulating means, the fourth sensor and the second image processing algorithm are configured to generate a hyperspectral image; for this purpose, the second manipulating means comprise a hyperspectral spectrometer. Thanks to the consideration of records taken in the region outside the visible spectrum, the records taken within the visible spectrum, i.e., the stereoscopic image, can be optimized by utilizing further image processing algorithms, e.g., for contrast enhancement or for intensification in case of low light. A preferred method for generating the hyperspectral image is spectral scanning. Here, monochromatic or nearly monochromatic images are recorded in succession for the various, very narrow-band wavelength regions; between the records, e.g., a tunable optical bandpass filter is set to the next wavelength range. This makes it possible for the hyperspectral camera in the sensor unit to be of a relatively compact design. Alternatively, however, other known methods for generating a hyperspectral image can be used, too; e.g., the snapshot method, or spatial scanning.

Preferably, the first and the second beam splitter are configured to be partially reflecting in the visual spectral region, and predominantly transmitting in the near infrared. The reverse configuration, with predominant transmission in the visible region and partial reflection in the near infrared, is feasible as well, according to the fabrication process. Especially for the case that ICG is used as a fluorescence marker, the first beam splitter is at least partially transparent to a first wavelength range between 650 nm and 900 nm, whereas the transmittance to wavelengths between 400 nm and 650 nm is less than 10%. With particular preference, the transmittance of the first beam splitter to wavelengths between 400 nm and 650 nm is less than 0.5%, while to wavelengths between 750 nm and 900 nm it is more than 95%.

Especially for the case that the second beam splitter is used together with a hyper spectrometer, the second spectral splitter shows has, for wavelengths between 700 nm and 1100 nm, a transmittance of more than 90%, or preferably nearly 100%, whereas in the wavelength range between 400 nm and 600 nm, the ratio between transmittance and reflectance is constant and may be, e.g., between 85:15 and 30:70, as, for example, 50:50.

This makes it possible, for example, that the first sensor unit can, together with the first manipulating means, the first sensor and the first image processing algorithm, be used for detecting the fluorescence spectrum of ICG and generating a corresponding fluorescence image. In that way, in addition to the stereoscopic image, a fluorescence image of the fluorescence spectrum of ICG and a hyperspectral image are generated. The two images mentioned last are monoscopic and are used, by way of further image processing algorithms, to improve the quality of presenting the stereoscopic image, or to display additional, complementary information. The representation of the complementary information can be superimposed on the stereoscopic image or displayed separately.

The radiation share split off for the visual region is preferably smaller than the share split off for the fluorescence image in the near infrared or for the hyperspectral image. Especially for the hyperspectral image, the light available is spectrally split up, for which reason a greater share of the radiation is required in this case. The beam splitters usable here are of the common dichroic type, e.g. glass disks introduced into the beam path at an angle of 45°. Alternatively, on can also use two prisms. The shares ratio of the light beam depends on the thickness of the coating and on the wavelength.

In another embodiment, at least one further beam splitter is arranged between at least one of the two beam splitters and one of the sensors allocated to this beam splitter, this at least further beam splitter deflecting light in a further light beam onto a further sensor. Moreover, further manipulating means are arranged between the further sensor and the further beam splitter. In that way, further analysis and/or imaging methods can be integrated, possibly in the form of a cascade of beam splitters. In this procedure, the methods that can do with light of lower intensity should be carried out at the end of the cascade.

As described above, the image processing unit is adapted to preferably employ data of the first and second monoscopic images for improving the quality of the stereoscopic image. Alternatively or additionally, a third monoscopic image can be generated that allows a different view of the object examined. A quality improvement is understood, in particular, the fact that the stereo image shows additional information that is complementary to the visual image. With the help of the two single images making up the stereoscopic image, one can, from a monoscopic image of a channel, generated with fluorescence signals, compute another monoscopic fluorescence image for the other channel, so that, then, a stereoscopic representation of the fluorescence is possible. The same applies to the images generated by other methods, e.g., the hyperspectral image. This contributes to the improved distinction and improved recognition of the state of the various tissue kinds; one can, for example, draw conclusions with regard to oncogenesis, perfusion, oxygen saturation, hemoglobin content, etc., because, on account of the fluorescence marking and the hyperspectral analysis, a variety of properties or parameters can be collected that are present in different tissue kinds in differing compositions. Examples of such parameters collectible are tissue oxygenation ($StO_2$), the perfusion index in the near infrared, the tissue hemoglobin index (THI), the tissue water index, TWI) or the tissue lipid index, LPI); on the basis of image analysis, the varied tissue kinds can be visualized in various ways.

The first sensor unit and/or the second sensor unit can preferably be configured as plug-in modules and be inserted into the appropriate endoscope body depending on the analysis or manipulation mode employed.

The stereo-endoscope described above can preferably be used for generating improved stereoscopic images of tissue samples, wherein a first monoscopic image I s generated by the detection of fluorescence signals in the infrared region, preferably such signals generated by the ICG dye, and a second monoscopic image is generated by the detection of a hyperspectral image, wherein the first and the second monoscopic image will be taken into account in an image processing operation for enhancing the contrast, and/or increasing the intensity, of the stereoscopic image.

It is to be understood that, within the scope of the present invention, the features mentioned before and those explained below are applicable not only in the combinations stated but also in other combinations or as stand-alone features.

Below, the invention will be explained in more detail and exemplified with reference to the accompanying drawings, which also show features essential to the invention, among others. These exemplary embodiments serve for illustration only and must not be interpreted as restrictive. For example, a description of an exemplary embodiment with a multitude of elements or components must not be interpreted as stating that all these elements or components are required for implementation. On the contrary, other exemplary embodiments may also contain alternative elements and components, or fewer elements or components. Elements or components of different exemplary embodiments may be combined with each other, unless stated otherwise. Modifications and variations described for one of the exemplary embodiments may also be applicable to other exemplary embodiments. To avoid redundancies, the same or corresponding elements in different figures are designated with the same reference numbers and are not explained more than once.

DETAILED DESCRIPTION

Figure 1:
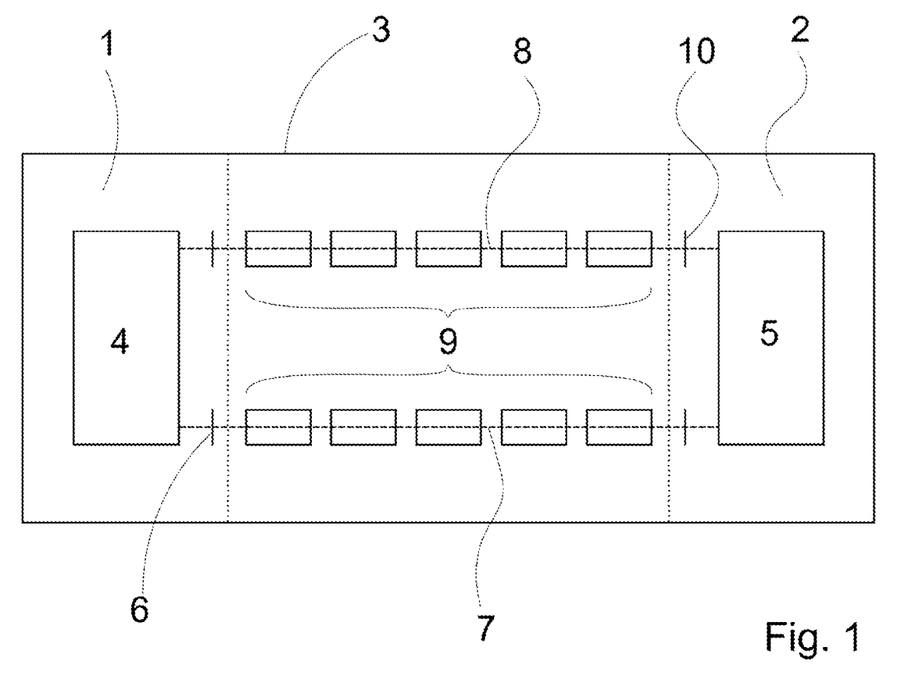
FIG. 1 shows the basic setup of a stereo-endoscope.

FIG. 1 shows the basic setup of a stereo-endoscope, the principle of which is known in prior art. The stereo-endoscope is made up of a distal end 1, a proximal end 2 and a shaft 3, which joins the distal end 1 to the proximal end 2. In FIG. 1, the physical separation of these major parts is indicated by the broken vertical lines. In addition to an input objective 4, the components arranged in the distal end 1 are light sources—not shown here—or at least light exit surfaces, which allow illumination of the object to be examined. Arranged in the proximal end 2 is an optical imaging device or system 5, in the simplest case, for example, in the form of a stereoscopic camera objective. The input objective 4 images the object in a first intermediate image plane 6, the imaging already being stereoscopic, i.e., taking place in a first optical imaging channel 7 and a second optical imaging channel 8. Here, the two optical channels 7, 8 are indicated by the broken horizontal lines. The shaft 3, which preferably is of a rigid design, contains an optical transmission system 9, which projects an intermediate image of the first intermediate image plane 6 onto a second intermediate image plane 10. From there, the image is projected by means of the optical imaging system 5 onto further optical elements—not shown here—for further use, i.e., analysis or manipulation. In case of a stereoscopic camera objective, the mage is projected onto flat-panel array detectors.

Figure 2:
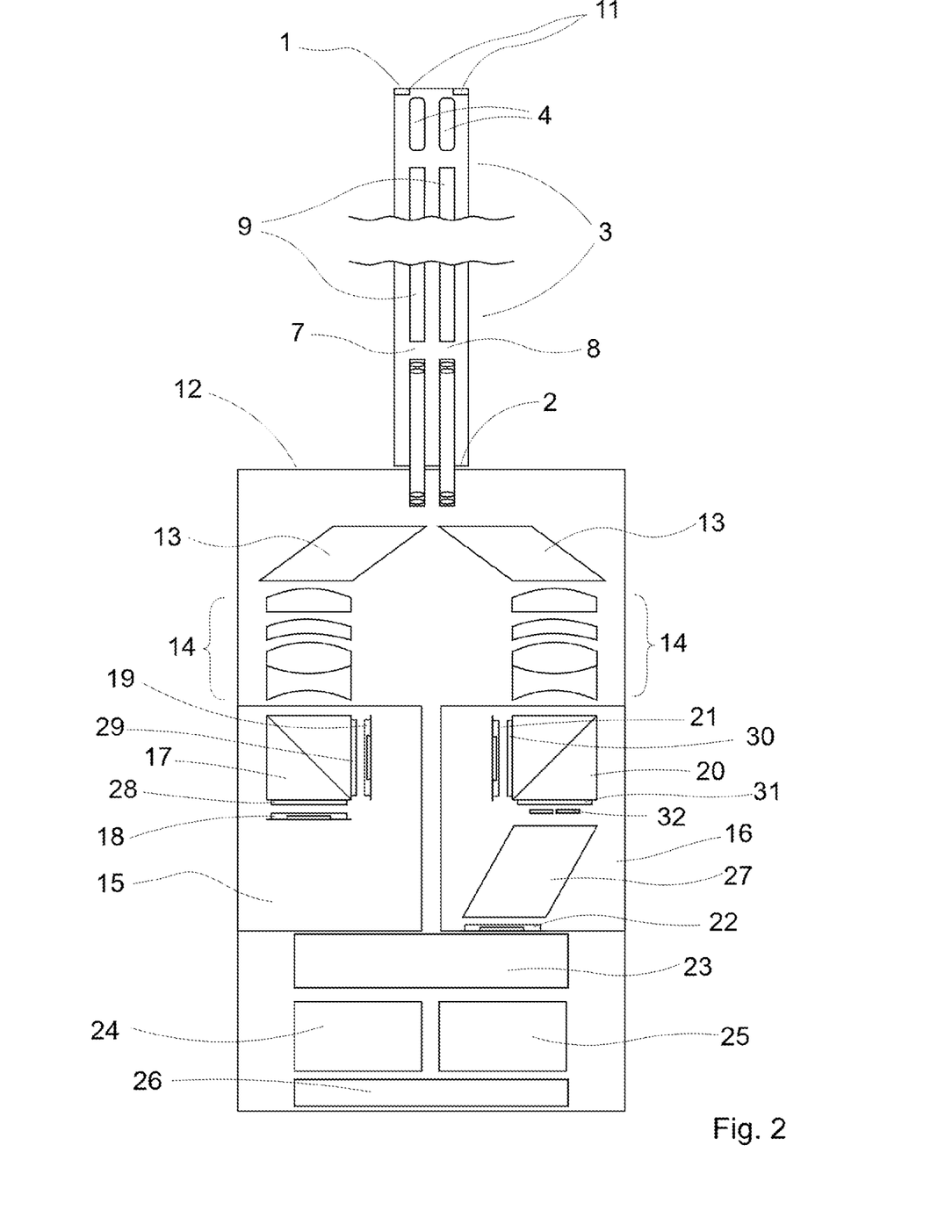
FIG. 2 shows a first embodiment of a stereo-endoscope,
FIG. 3 shoes a second embodiment of a stereo-endoscope.

The configuration shown in FIG. 2 uses different objectives 4, and each of the images is transmitted from the distal end 1 to the proximal end 2 in a separate channel, i.e., the first optical imaging channel 7 and the second optical imaging channel 8. Alternatively, transmission can take place in a single channel, either with two images being imaged by means of two objectives 4, or with two superimposed images being imaged and transmitted by means of a single objective, and with a separation into two imaging channels with two single images taking place only by means of a pupil separation at the end of the transmission system 9 in the optical imaging system 5.

While the stereoscopic image in the visual region, which comprises wavelengths in the range from about 380 nm up to 780 nm, shows significant information and yields the surgeon a good overall view of the tissue to be treated, even more detailed information can be visualized by means of special methods, e.g., the marking of tissue with fluorescent dyes, enabling the surgeon to carry out more precise planning of the operation and a better delimitation, e.g., of the tissue parts that are affected by malignant tumors and are to be removed.

The stereo-endoscopes presented below make it possible, in addition to the stereoscopic image in the visual region, to record or generate further monoscopic images containing image information complementary to the stereoscopic image, and, where necessary, to take them into account in the calculation of the stereoscopic image in order to obtain a representation of all image information in one image. The term "complementary image information" is understood to define image information that was invisible in the original stereoscopic image, whether due to the simple imaging without manipulation or because of the restricted spectral region. The complementary image information supplements the image information of the stereoscopic image but is not redundant. Thus, methods yielding complementary image information are complementary in principle.

FIG. 2 shows a first embodiment of a stereo-endoscope. Identical reference numbers correspond to the same elements as in other figures and may not be explained again. At the distal end 1 of the shaft 3 here, illuminating means 11 are shown in addition. These means may be light sources such as, e.g., LEDs, which are employed directly at the distal end 1. Advantageously, however, the illuminating means 11 are the ends of light guide fibers, from which light is coupled out. This makes it possible to arrange the illuminating means outside the shaft 3, permitting easier change to another kind of illumination or replacement in case of failure. Moreover, this prevents heat generation at the distal end 1. Finally, this also allows the use of larger light sources, e.g., such that radiate monochromatic coherent light.

Arranged at the proximal end 2 of the shaft 3 is an analysis unit 12, which may, e.g., be integrated in the body or housing of the endoscope. The shaft 3 including the optical elements used therein may correspond, e.g., to that described in the applicant's DE 10 2017 113 274 A1. In the present case, the optical transmission system 9 or the imaging system 5, which for clarity's sake is not shown in FIG. 2, projects the light transmitted via the shaft 3 from the distal end 1 to the proximal end 2, where that light is imaged not onto a flat-panel array detector of a camera but onto prisms 13, which offset the light beams relative to each other so as to increase their mutual distance and gain more space for manipulations of the light beams. On the output side of the prisms 13, the light beams are directed onto adapter optics 14, which here, for example, are represented by a combination of lenses, to which, however, the configuration of the adapter optics 14 is not restricted. Light from the first imaging channel 7 is projected into a first sensor unit 15 via one of the adapter optics 14. Light from the second imaging channel 8 is projected into a second sensor unit 16 via the other of the adapter optics 14.

The first sensor unit 15 comprises a first beam splitter 17, which splits the light into a first light beam 41 and a second light beam 42. The first sensor unit 15 further comprises a first sensor 18 and a second sensor 19. The first sensor 18 detects light of the first light beam 41 and converts it into first electromagnetic signals; the second sensor 19 detects light of the second light beam 42 and converts it into second electromagnetic signals.

The second sensor unit 16 comprises a second beam splitter 20, which splits the light into a third light beam 43 and a fourth light beam 44. The second sensor unit 16 further comprises a third sensor 21, which detects light of the third light beam 43 and converts it into third electromagnetic signals, and a fourth sensor 22, which detects light of the fourth light beam 44 and converts it into fourth electromagnetic signals.

Without loss of generality, the second sensor 19 and the third sensor 21 in the example shown here are of the same kind, detecting light in the visual region. i.e., in the spectral region between 380 nm and about 780 nm that is visible to the human eye. In principle, an allocation to, or combination of, other paths is also possible. The first to fourth electromagnetic signals are processed in an image processing unit 23, with the second and third electromagnetic signals being processed into a stereoscopic image.

Figure 4:
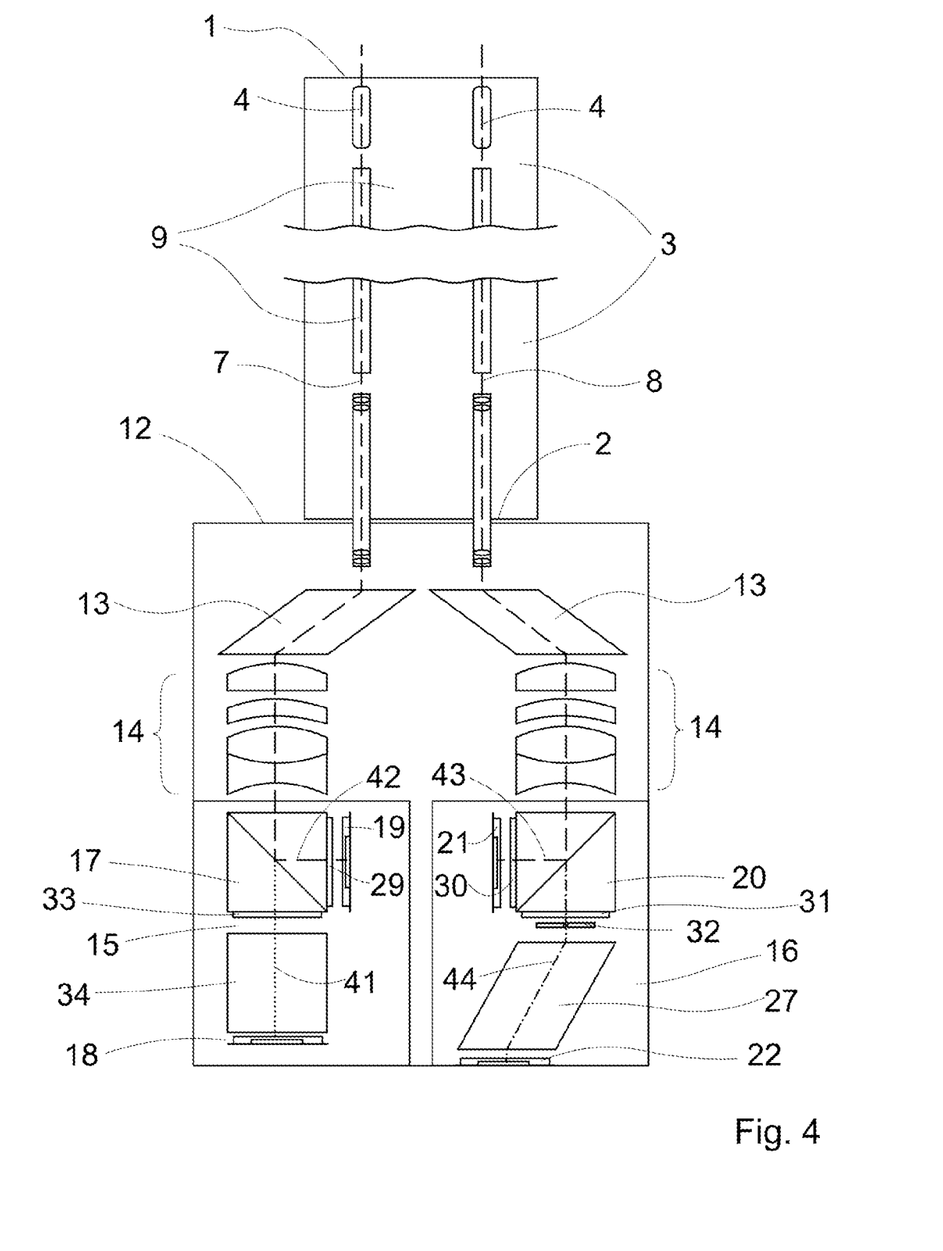
FIG. 4 shows the second embodiment with the arrangement of light paths.

The light paths and light beams are presented in detail in FIG. 4, which shows a segment of an endoscope. The second and the third light beam 42, 43 are both shown as broken lines, as they hit the same kind of detectors. The first light beam 41 is shown as a dotted line, and the fourth light beam 44 as a dash-and-dot line.

To obtain as much complementary information about the object examined as possible, the first light beam 41 and the fourth light beam 44 are manipulated or analyzed in ways different from each other. The methods by which these two light beams are manipulated or analyzed differ from each other and are selected in such a way that they supply image information complementary to the stereoscopic image and to each other. Advantageously, also the first beam splitter 17 and the second beam splitter 20 differ in their properties. This is not compelling, though, if the methods by which the first light beam 41 and the fourth light beam 44 are manipulated or analyzed supply complementary image information even with beam splitters of identical configuration.

Accordingly, in the first sensor unit 15 between the first beam splitter 17 and the first sensor 18, first manipulating means are arranged with which the first light beam 41 is manipulated, whereas between the second beam splitter 20 and the fourth sensor 22, second manipulating means are arranged with which the fourth light beam 44 is manipulated. Therein, first manipulating means and second manipulating means differ from each other. In the simplest case, the manipulating means comprise simple filters, with which, for example, the visible light is blocked, and light is transmitted only in the near infrared, the far infrared and/or the ultraviolet spectral region.

Additionally implemented in the image processing unit 23 are appropriate image processing algorithms tuned to the manipulating means. Implemented are, in concrete terms, a first image processing algorithm tuned to the first manipulating means, and a second image processing algorithm tuned to the second manipulating means. The first image processing algorithm generates a first monoscopic image, while the second image processing algorithm generates a second monoscopic image. The first and second image processing algorithms, the first and second manipulating means, and the first and fourth sensors 18, 22 are specified so that the first and second monoscopic images and the stereoscopic image contain complementary image information. The first and fourth sensors 18, 22 may also be equal, if the manipulating means and/or image still satisfy the condition that complementary image information is generated.

The image information of the stereoscopic image can then be supplemented by the image information of one or both of the two monoscopic images, so that one obtains an augmented image, which thanks to the complementary information has a markedly higher information content than the stereoscopic image alone. The supplementation of the information, or the superimposition of all image information can also be performed image processing unit 23. Generally, the image processing unit 23 is adapted to use or to take into account data of the first and of the second monoscopic image for improving the quality of the stereoscopic image, or for generating a third monoscopic image. The image processing unit 23 may be arranged within the body or housing of the endoscope. Advantageously, however, it is arranged outside and physically separated from the endoscope, in order to keep the space occupied by the endoscope small on the one hand, and to reduce heat generation in and around the endoscope on the other hand.

The analysis unit 12 contains, in addition, further elements: a first control unit 24, with which the first sensor unit is controlled, and a second control unit 25, with which the second sensor unit is controlled. Like the image processing unit 23, the control units 24 and 25 may be arranged within, or preferably outside, the housing. In addition, these control units 24 and 25 can be used to control the illumination, if, for example, light of other wavelengths in addition to visible light is to be coupled into both imaging channels 7 and 8, with this additional light differing for the imaging channels 7 and 8. Moreover, the analysis unit 12 contains a connecting interface 26, which, among other functions, serves for power supply and for the transfer of data and control signals. It may also serve for light incoupling if the light sources are arranged, for example, outside the analysis unit 12 or not at the distal end 1 of the shaft 3, which is the case, e.g., if the illuminating means comprises several, at least 2 light sources and at least one of the light sources is configured to radiate monochromatic coherent light.

While, in the embodiment shown here, the image processing unit 23 and the control units 24 and 25 are arranged in the analysis unit 12, this arrangement is not absolutely imperative. Both the control units 24 and 25 and the image processing unit 23 may also be arranged outside the analysis unit 12. In particular, the image processing unit 23 may be part of a computer arranged in the periphery of a robotic surgery system. The first control unit 24 and the second control unit 25 are shown as separate units here, but they can also be combined in a single unit, in which case the control unit would be connected with the first sensor unit 15 and the second sensor unit 16 via separate output ports. In a preferred embodiment, the first sensor unit 15 and the second sensor unit 16 may be configured as plug-in modules, so that it is easier to alternate between different manipulation or analysis methods, which merely requires the plug-in modules in the analysis unit 12 to be changed. The plug-in modules may be provided with identification codes, so that, via the control units 24 and 25, the image processing unit 23 automatically recognizes which plug-in module is plugged in the analysis unit 12, and selects a corresponding image processing algorithm.

The first and second manipulating means, the first and fourth sensors 18 and 22, and the first and second image processing algorithms, then, are configured to generate image information that is complementary to each other and to the information content of the stereoscopic image. In particular, they may be adapted to alternatively generate a fluorescence image of fluorescence signals in the infrared region, a hyperspectral image, a polarization-resolved image, a Raman spectroscopy image, an optical-coherence tomography image, a speckle contrast image, a multiband image or a narrowband image.

In the embodiment shown in FIG. 2, the first manipulating means, the first sensor 18 and the first image processing algorithm are adapted to generate a fluorescence image of fluorescence signals in the infrared region, whereas the second manipulating means, the fourth sensor 22 and the second image processing algorithm are adapted to generate a hyperspectral image. For that purpose, the second manipulating means comprise a hyperspectral spectrometer 27. Here, for the improved generation of complementary information, also the first beam splitter 17 and the second beam splitter 20 are configured differently, with the first beam splitter 17 being selected to have, in the configuration shown here, the highest possible transmittance to the fluorescence signals. Which fluorescence signals are to be detected depends, of course, on the fluorescence markers used. Here, without loss of generality, the first sensor is meant to be configured for the detection of the fluorescence spectrum of ICG. The emission wavelength of ICG has a maximum at 830 nm; therefore, the first sensor 18 is adapted to be capable of detecting electromagnetical radiation of this wavelength. Here, the first light beam 41 is additionally filtered by a first filter 28, which is adapted to the emission wavelength of ICG and transmits light in the wavelength range of, e.g., 810 to 850 nm. The Semrock filter FF01-832/3725 may be used therefore, for example. Arranged in front of the second sensor 19 is a second filter 29, which blocks light outside the visible region, i.e., ultraviolet and infrared light. A filter eligible therefore is Edmund #89-794. Arranged in front of the third sensor 21 is a third filter 30, which is configured identically to the second filter 29. In principle, the use of filters is optional. Depending on the method employed, the coating of the beam splitter may suffice to perform an appropriate spectral separation—which corresponds to a filtering—of the light.

As already mentioned farther above, another complementary method employed using the second sensor unit16 is a hyperspectral analysis of the fourth light beam 44, wherein it is of advantage if the second beam splitter 20 has a high transmittance not only of more than 90% in the infrared spectral region above 700 nm, but also of preferably more than 50% up to 80% in the visible spectral region. The reason for this is that the light available in the hyperspectral spectrometer 27 is spectrally dispersed, whereby effectively a lot less intensity is available to each wavelength range, so that a greater share of the radiation is required here.

Arranged at the output end of the beam splitter 20, between this and the hyperspectrometer, is first a yellow filter 31, e.g., the Schott filter GG495. Here, in connection with the hyperspectral analysis with the help of a grating, the filter serves to suppress longer wavelengths and, thus, to block higher orders in the grating spectrometer. Having passed the filter, the light enters the hyperspectral spectrometer 27 through a slit 32.

The two beam splitters 17 and 20 may be configured as simple glass discs with dichroic effect. In the present example, however, each of them consists of two prisms assembled in the shape of a cube or a rectangular parallelepiped, which is of advantage for avoiding imaging aberrations. On their light input side, both the first beam splitter 17 and the second beam splitter 20 are provided with antireflection coating for the wavelength range between 400 nm and 1100 nm, as a precaution against light loss. On their sides facing the second sensor 19 and the third sensor 21, the two beam splitters are blackened. Both the blackening and the antireflection coating serve the purpose of reducing or avoiding stray light. In the case of a simple configuration as glass discs, these would be arranged along the diagonals shown here—the interface between the two prisms, which constitutes the beam-splitting coating proper, or the beam splitter—i.e., at an angle of 45° relative to the direction of incidence of the respective light beam.

In the configuration shown here, the first beam splitter 17 and the second beam splitter 20 are partially reflective in the visual spectral region and predominantly transmissive in the near infrared. Here, the first beam splitter 17 is preferably at least partially transparent in a first wavelength range between 650 nm and 900 nm. The transmittance in the near infrared, comprising the wavelength range between 750 nm and 900 nm, is higher than 90%, preferably higher than 95%, whereas with wavelengths between 400 nm and 650 nm, the transmittance is lower than 10%, preferably lower than 1% or with particular preference, lower than 0.5%. The second beam splitter 20, especially in connection with the generation of hyperspectral images, has ideally a transmittance of nearly 100% to wavelengths between 700 nm and 1100 nm, whereas, in the 400 nm to 600 nm wavelength range, the ratio of transmittance to reflectance is between 80:20 and 50:50 and preferably does not fluctuate, i.e. is constant. The splitting ratio is a function of the buildup and/or composition of the coat, and of the wavelength.

The endoscope generates a first monoscopic image on the basis of the signals read from the first sensor 18, and a second monoscopic image on the basis of the signals read from the fourth sensor 22. The image processing unit 23, then, can use the data of the first and second monoscopic images for improving the quality of the stereoscopic image, or—as an alternative or supplement—for generating a third monoscopic image, which will be displayed then to a viewer in addition. Instead of a stereoscopic image it is also possible to present two monoscopic images, depending on the surgeon's requirements. These monoscopic images already exist, as the stereoscopic image results from the composition of two monoscopic images.

Figure 3:
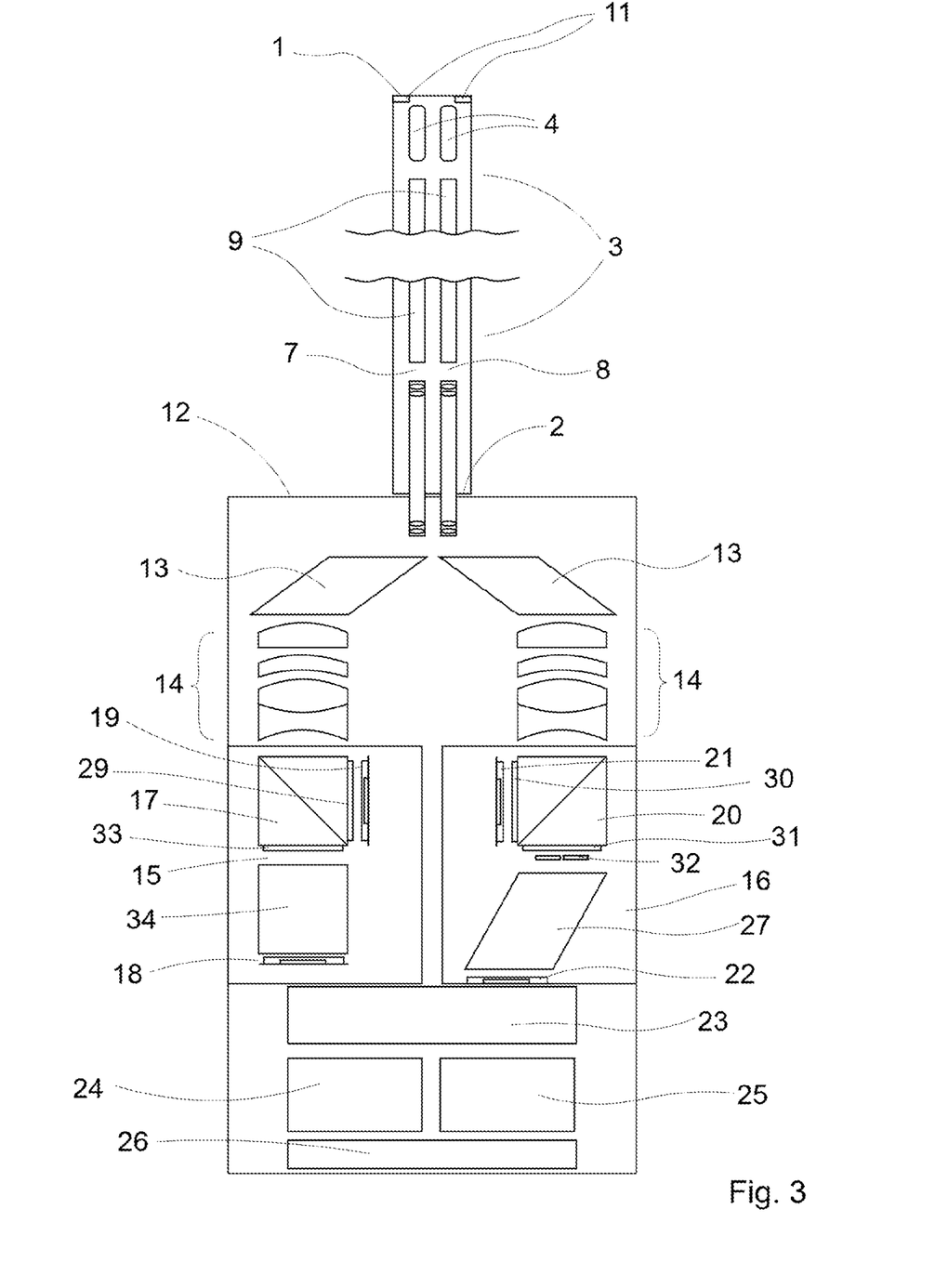

A variation of the stereo-endoscope shown in FIG. 2 is shown in FIG. 3, in which the first manipulating means, the first sensor 18 and the first image processing algorithm are specified so as to generate a multiband image. Instead of the first filter 28 in FIG. 2, a band-pass filter 33 is used here, which is transmissive to several narrow spectral ranges. It is used in combination with a narrow-band light source that emits light in several spectral ranges in which the band-pass filter 33 is transmissive. In a spectrometer unit 34, the light is spectrally dispersed in accordance to the number of bands. In this case, the first sensor 18 can be controlled in such a way that, e.g., that adjacent pixels react to certain, mutually differing spectral ranges in which the band-pass filter 33 is transmissive. Alternatively, the spectrometer unit 34 may be configured to generate on its output side a number of images corresponding to the number of bands, each of which corresponds to a band and is imaged in a separate area of the first sensor 18.

In principle, it is also possible to arrange, between at least one of the two beam splitters and one of the sensors allocated to this beam splitter, at least one further beam splitter (not shown here), which deflects light in a further light beam onto a further sensor; in connection therewith, further manipulating means are arranged between the further sensor and the further beam splitter. In that way, a cascade of beam splitters and different manipulation or analysis methods can be implemented.

Thus, the stereo-endoscope described above can be used to generate improved stereoscopic images of tissue samples. If, for example, a first monoscopic image is generated by detecting fluorescence signals in the infrared region, and a second monoscopic image is generated by detecting a hyperspectral image, the two monoscopic images can be taken into account within the scope of an image processing operation, e.g., for enhancing the contrast and/or increasing the intensity of the stereoscopic image; in addition, due to the complementary analysis methods, further information can be taken up by the stereoscopic image. In that way, a surgeon using a robotic operating system obtains more detailed information, e.g., about the tissue to be removed, and can plan his operation more precisely. Also, operations such as tumor removing will become less error-prone as regards the differentiation of healthy and afflicted tissue.

LIST OF REFERENCE NUMBERS 1 distal end
2 proximal end
3 shaft
4 input objective
5 optical imaging system
6 first intermediate image plane
7 first imaging channel
8 second imaging channel
9 optical transmittance system
10 second intermediate image plane
11 illuminating means
12 analysis unit
13 prism
14 adapter optics
15 first sensor unit
16 second sensor unit
17 first beam splitter
18 first sensor
19 second sensor
20 second beam splitter
21 third sensor
22 fourth sensor
23 image processing unit
24 first control unit
25 second control unit
26 connecting interface
27 hyperspectral spectrometer
28 first filter
29 second filter
30 third filter
31 yellow filter
32 slit
33 band-pass filter
34 spectrometer unit
41 first light beam
42 second light beam
43 third light beam
44 fourth light beam

What is claimed is:

1. A stereo-endoscope for observing and analyzing an object, comprising:
    a shaft with a distal end and a proximal end,
    an illumination device configured to illuminate the object from the distal end of the shaft,
    a stereoscopic imaging device which transmits light radiated by the object from the distal end to the proximal end,
    a first sensor unit upon which light from a first imaging channel is imaged, wherein the first sensor unit comprises a first beam splitter which splits the light into a first light beam and a second light beam, and a first sensor and a second sensor which detect light of the first light beam and the second light beam, respectively, and convert it into first and second electromagnetic signals, respectively,
    and a second sensor unit upon which light from a second imaging channel is imaged, wherein the second sensor unit comprises a second beam splitter which splits the light into a third light beam and a fourth light beam, and a third sensor and a fourth sensor, which detect light of the third light beam and the fourth light beam, respectively, and convert it into third and fourth electromagnetic signals, respectively,
    wherein the second sensor and the third sensor are of the same kind and each detect light in the visible spectral region,
    an image processing unit for processing the first through the fourth electromagnetic signals, processing the second and third electromagnetic signals into a stereoscopic image,
    wherein:
    in the first sensor unit, between the first beam splitter and the first sensor a first manipulating device is arranged with which the first light beam is manipulated,
    in the second sensor unit, between the second beam splitter and the fourth sensor, a second manipulating device, differing from the first one, is arranged, with which the fourth light beam is manipulated,
    in the image processing unit, there are implemented a first image processing algorithm that is tuned to the first manipulating device and generates a first monoscopic image, and a second image processing algorithm that is tuned to the second manipulating device and generates a second monoscopic image, and
    the first and second manipulating devices, the first sensor and the fourth sensor and the first and second image processing algorithms are specified in such a way that the first and second monoscopic images and the stereoscopic image contain complementary image information derived from mutually complementary imaging methods.

2. The stereo-endoscope as claimed in claim 1, wherein the illuminating device comprises a plurality of light sources, including at least a first and a second light source, of which at least one light source is adapted to radiate monochromatic, coherent light.

3. The stereo-endoscope as claimed in claim 1, wherein the first and second manipulating devices, the first sensor and the fourth sensor, and the first and second image processing algorithms are alternatively adapted to generate:
    a fluorescence image from fluorescence signals,
    a hyperspectral image,
    a polarization-resolved image,
    a Raman spectroscopy image,
    an optical coherence tomography image,
    a speckle contrast image,
    a multiband image, or
    a narrowband image.

4. The stereo-endoscope as claimed in claim 1, wherein the first beam splitter and the second beam splitter differ in their configurations.

5. The stereo-endoscope as claimed in claim 1, wherein the first manipulating deice, the first sensor and the first image processing algorithm are adapted to generate a fluorescence image from fluorescence signals in an infrared region, and the first sensor is adapted to detect the fluorescence spectrum of ICG (indocyanine green).

6. The stereo-endoscope as claimed in claim 1, wherein the second manipulating device, the fourth sensor and the second image processing algorithm are adapted to generate a hyperspectral image, and the second manipulating device comprises a hyperspectral spectrometer.

7. The stereo-endoscope as claimed in claim 1, wherein the first beam splitter and the second beam splitter are adapted either to be partially reflective in the visual spectral region and predominantly transmissive in the near infrared region, or predominantly transmissive in the visual spectral region and partially reflective in the near infrared region.

8. The stereo-endoscope as claimed in claim 7, wherein the first beam splitter is at least partially transparent in a first wavelength range between 650 nm and 900 nm, and the transmittance for wavelengths between 400 nm and 650 nm is less than 10%.

9. The stereo-endoscope as claimed in claim 7, wherein the transmittance of the first beam splitter for wavelengths between 400 nm and 650 nm is lower than 0.5% and for wavelengths between 750 nm and 900 nm is higher than 95%.

10. The stereo-endoscope as claimed in claim 7, wherein the second beam splitter for wavelengths between 700 nm and 1100 nm has a transmittance of higher than 90%, or preferably of almost 100%.

11. The stereo-endoscope as claimed in claim 10, wherein, in the second beam splitter, the proportion of transmittance and reflectance in the wavelength range between 400 nm and 600 nm is constantly between 80:20 and 50:50.

12. The stereo-endoscope as claimed in claim 1, wherein between at least one of the two beam splitters and one of the sensors assigned to this beam splitter, at least one further beam splitter is arranged, which deflects light in another light beam upon a further sensor, and a further manipulating device is arranged between the further sensor and the further beam splitter.

13. The stereo-endoscope as claimed in claim 1, wherein the image processing unit is designed to use data of the first and of the second monoscopic image for improving quality of the stereoscopic image or to generate a third monoscopic image.

14. The stereo-endoscope as claimed in claim 1, wherein the first sensor unit and the second sensor unit are configured as plug-in modules.

15. A use of a stereo-endoscope as claimed in claim 1 for generating improved stereoscopic images of tissue samples, wherein a first monoscopic image is generated by detection of fluorescence signals, and a second monoscopic image is generated by detection of a hyperspectral image, wherein the stereoscopic image takes account of the first and the second monoscopic image in an image processing operation for contrast enhancement and/or intensity increase and/or improved differentiation of tissue.

* * * * *